(12) United States Patent
Kaneko et al.

(10) Patent No.: US 7,579,485 B2
(45) Date of Patent: Aug. 25, 2009

(54) PROCESS FOR PRODUCING LACTONE

(75) Inventors: Makoto Kaneko, Yokohama (JP); Yasuhiro Ninomiya, Yokohama (JP); Tetsuji Nakamura, Yokohama (JP); Eiji Satou, Yokohama (JP)

(73) Assignee: Mitsubishi Rayon Co., Ltd., Tokyo (JP)

( * ) Notice: Subject to any disclaimer, the term of this patent is extended or adjusted under 35 U.S.C. 154(b) by 693 days.

(21) Appl. No.: 10/502,595

(22) PCT Filed: Feb. 3, 2003

(86) PCT No.: PCT/JP03/01060

§ 371 (c)(1),
(2), (4) Date: Jul. 27, 2004

(87) PCT Pub. No.: WO03/066617

PCT Pub. Date: Aug. 14, 2003

(65) Prior Publication Data

US 2005/0080276 A1 Apr. 14, 2005

(30) Foreign Application Priority Data

Feb. 8, 2002 (JP) .............................. 2002-032715

(51) Int. Cl.
*C07D 307/02* (2006.01)
(52) U.S. Cl. .................................... 549/295
(58) Field of Classification Search ................ 549/273, 549/295
See application file for complete search history.

(56) References Cited

U.S. PATENT DOCUMENTS 4,588,820 A    5/1986  Stokker

FOREIGN PATENT DOCUMENTS

| EP | 1 052 258 A1 | 11/2000 |
| GB | 865310 | 4/1961 |
| GB | 1 367 435 | 9/1974 |
| JP | 3014171 | 12/1999 |

OTHER PUBLICATIONS

Barton et al., Journal of the Chemical Society, "Photochemical transformations. XVI. A novel synthesis of lactones", 1965, pp. 181-190.*
Osamu Kanno, et al., "Efficient syntheses of (S)-4-hydroxy-2-pyrrolidinone derivatives", Heterocycles, vol. 53, No. 1, pp. 173-181 2000.
Patent Abstracts of Japan, JP 04-365491, Dec. 17, 1992.
Wan Yong Lou, et al., "Research Progress on Enzymatic Hydrolysis of Nitrile", 28(6), 2001, pp. 76-81 (with English Abstract).

* cited by examiner

*Primary Examiner*—D. Margaret Seaman
*Assistant Examiner*—Niloofar Rahmani
(74) *Attorney, Agent, or Firm*—Oblon, Spivak, McClelland, Maier & Neustadt, P.C.

(57) ABSTRACT

A method for producing lactones, which comprises reacting an amide compound of Formula (I):

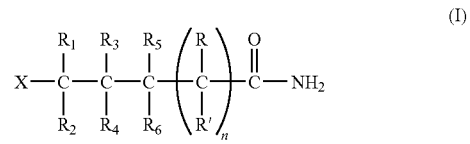

[wherein X represents a halogen atom; R, R' and $R_1$ to $R_6$ each independently represents a hydrogen atom or any desired substituent; and n represents an integer of 0 to 2] with an aqueous medium.

15 Claims, No Drawings

PROCESS FOR PRODUCING LACTONE

TECHNICAL FIELD

The present invention relates to a method for producing lactones. Lactones are useful as starting materials or solvents for synthesis of various compounds, such as pharmaceutical preparations and agricultural chemicals, etc.

BACKGROUND ART

A lactone is a cyclic compound containing an ester group in the ring, and those having 3, 4, 5, 6 and 7 ring members are referred to as α-, β-, γ-, δ- and ε-lactones, respectively. Many strategies are known for synthesis of lactones, including those using an acid catalyst to synthesize γ-butyrolactones from 4-hydroxybutyric acids, as well as those involving, e.g., reduction of succinic anhydrides or heating of 4-halogenated butyric acids to synthesize γ-butyrolactones.

However, although depending on the types of γ-butyrolactones to be produced, most of these strategies are associated with problems such as formation of byproducts, low yield, risks of explosion, and difficult synthesis of starting materials. Thus, there has been a strong need to develop a novel synthesis method.

To produce 3-hydroxy-γ-butyrolactones by organic synthesis, for example, glycidol and carbon monoxide may be reacted at elevated temperature and pressure in the presence of a noble metal catalyst (U.S. Pat. No. 4,968,817), or 3-butenoic acid may be epoxidized by treatment with hydrogen peroxide in the presence of a platinum catalyst and then hydrated and converted into a lactone (Angew. chem., Int. Ed. Eng 994-1000 (1966)). However, these methods are associated with increased risks of explosion, etc. Also known are a 7-step process starting with L-ascorbic acid or D-isoascorbic acid (Synthesis 570-572 (1987)) and a 3-step process starting with L-malic acid (JP-A-6-172256). However, these processes require complicated procedures and also fail to produce successful results in terms of yield because they involve multi-step reactions.

In addition, 3-hydroxy-γ-butyrolactones are known to be produced by biological processes using *Pseudomonas* or *Enterobacter* bacteria as a microbial catalyst to produce (S)-3-hydroxy-γ-butyrolactone from ethyl 4-chloro-3-hydroxybutyrate [see, e.g., Tetrahedr. Asym. 11. 3109-3112 (1996)]. However, such biological processes are not successful in terms of enzyme stability. Also, they cannot be regarded as industrially advantageous because complicated procedures are required to prepare substrates.

DISCLOSURE OF THE INVENTION

The object of the present invention is to provide an industrially advantageous method for producing lactones, particularly γ-butyrolactones or δ-valerolactones, starting with easily synthesizable amides. This method can be carried out under mild conditions and reduce steps and the risk of byproduct formation.

As a result of extensive and intensive efforts made to overcome the problems stated above, the inventors of the present invention have surprisingly found that the reaction between 4-halo-butylamides and water causes rapid elimination of halogen and ammonia to give corresponding γ-butyrolactones in high yield. This finding led to the completion of the present invention.

Namely, the present invention is directed to a method for producing lactones, which comprises reacting an amide compound of Formula (I):

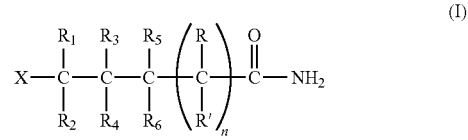

[wherein X represents a halogen atom; R, R' and $R_1$ to $R_6$ each independently represents a hydrogen atom or any desired substituent; and n represents an integer of 0 to 2] with an aqueous medium.

Also, the present invention is directed to a method for producing γ-butyrolactones, which comprises reacting a 4-halo-butylamide of Formula (II):

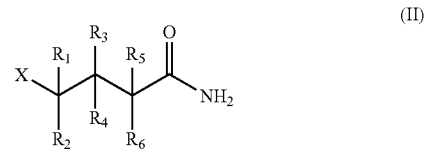

[wherein X represents a halogen atom, and $R_1$ to $R_6$ each independently represents a hydrogen atom or any desired substituent] with an aqueous medium to give a γ-butyrolactone of Formula (III):

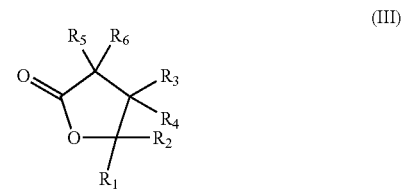

[wherein $R_1$ to $R_6$ each independently represents a hydrogen atom or any desired substituent].

In the above method, the 4-halo-butylamide of Formula (II) may be, for example, a 4-halo-3-hydroxybutylamide. Examples of the compound represented by Formula (II) include those obtained by nitrile hydratase treatment of a 4-halo-butyronitrile having Formula (IV):

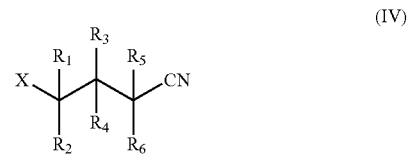

[wherein X represents a halogen atom, and $R_1$ to $R_6$ each independently represents a hydrogen atom or any desired substituent]. The phrase "nitrile hydratase treatment" is intended to mean hydration by the catalytic action of nitrile hydratase.

Examples of nitrile hydratase as used herein include those produced by at least one microorganism belonging to any genus selected from the group consisting of *Arthrobacter, Brevibacterium, Caseobacter, Corynebacterium, Pseudomonas* and *Rhodococcus* or those produced by mixed microorganisms composed of at least one microorganism belonging to one genus selected from the group listed above and at least one microorganism belonging to another genus selected from the group listed above. Alternatively, nitrile hydratase may be produced by transformants carrying a gene encoding nitrile hydratase.

Further, the present invention is directed to a method for producing δ-valerolactones, which comprises reacting a 5-halo-pentylamide of Formula (V):

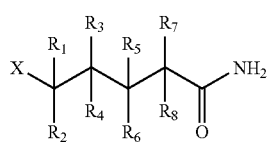

(V)

[wherein X represents a halogen atom, and $R_1$ to $R_8$ each independently represents a hydrogen atom or any desired substituent] with an aqueous medium to give a δ-valerolactone of Formula (VI):

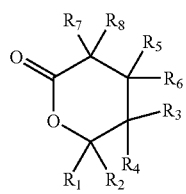

(VI)

[wherein $R_1$ to $R_8$ each independently represents a hydrogen atom or any desired substituent].

In the above method, the reaction may be carried out, for example, at a temperature of 30° C. to 100° C. and at a pH of 1.0 to 6.0.

The present invention will be described in more detail below.

The present invention aims to effect a reaction between an amide compound of the above Formula (I) and an aqueous medium to cause elimination of halogen and ammonia, thereby obtaining lactones of interest. The present invention enables the provision of a fewer-step and higher-yield method for producing lactones. In particular, it is beyond all expectations that γ-butyrolactones could be produced from 4-halobutylamides.

In Formula (I), n represents an integer of 0 to 2 and X represents a halogen atom. A halogen atom is intended to mean a fluorine atom, a chlorine atom, a bromine atom or an iodine atom, with a chlorine atom being preferred. When n is 0, the amide compound to be used as a starting material is a 4-halo-butylamide of Formula (II):

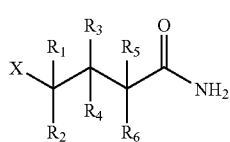

(II)

and the resulting lactone is a γ-butyrolactone of Formula (III):

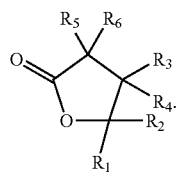

(III)

When n is 1, the amide compound to be used as a starting material is a 5-halo-pentylamide of Formula (V):

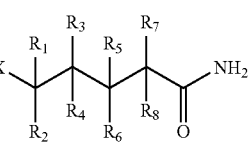

(V)

and the resulting lactone is a δ-valerolactone of Formula (VI):

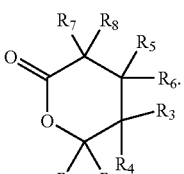

(VI)

Likewise, when n is 2, the amide compound to be used as a starting material is a 6-halo-hexylamide and the resulting lactone is an ε-caprolactone.

In Formulae (I) to (VI), $R_1$ to $R_8$ as well as R and R' (when n=1 in Formula (I), R and R' correspond to $R_7$ and $R_8$, respectively) may be the same or different and each independently represents a hydrogen atom or any desired substituent. The term "any desired substituent" as used herein is intended to mean an optionally substituted $C_1$-$C_{20}$ hydrocarbon group (i.e., containing 1 to 20 carbon atoms), an optionally substituted $C_1$-$C_{20}$ alkoxy group (i.e., containing 1 to 20 carbon atoms), an optionally substituted $C_6$-$C_{20}$ aryloxy group (i.e., containing 6 to 20 carbon atoms), an optionally substituted $C_7$-$C_{20}$ alkylaryloxy group (i.e., containing 7 to 20 carbon atoms), an optionally substituted $C_2$-$C_{20}$ alkoxycarbonyl group (i.e., containing 2 to 20 carbon atoms), an optionally substituted amino group, an optionally substituted silyl group or a hydroxyl group. Alternatively, it may be an optionally substituted alkylthio group, an optionally substituted arylthio group, an optionally substituted alkylsulfonyl group or an optionally substituted arylsulfonyl group.

Such a hydrocarbon group may be either a saturated or unsaturated acyclic (open chain) group or a saturated or unsaturated cyclic group. In a case where the hydrocarbon group is acyclic, it may be either linear or branched. Examples of such a hydrocarbon group include a $C_1$-$C_{20}$ alkyl group, a $C_2$-$C_{20}$ alkenyl group, a $C_2$-$C_{20}$ alkynyl group, a $C_4$-$C_{20}$ alkyldienyl group, a $C_6$-$C_{18}$ aryl group, a $C_6$-$C_{20}$ alkylaryl group, a $C_6$-$C_{20}$ arylalkyl group, a $C_4$-$C_{20}$ cycloalkyl group, a $C_4$-$C_{20}$ cycloalkenyl group and a ($C_3$-$C_{10}$ cycloalkyl)-$C_1$-$C_{10}$ alkyl group.

The $C_1$-$C_{20}$ alkyl group is preferably a $C_1$-$C_{10}$ alkyl group. Examples of such an alkyl group include, for example, a methyl group, an ethyl group, a propyl group, an isopropyl group, an n-butyl group, a sec-butyl group, a tert-butyl group, a pentyl group, a hexyl group, an octyl group, a nonyl group, a decyl group, a undecyl group and a dodecyl group.

The $C_2$-$C_{20}$ alkenyl group is preferably a $C_2$-$C_{10}$ alkenyl group. Examples of such an alkenyl group include, for example, a vinyl group, an allyl group, a propenyl group, an isopropenyl group, a 2-methyl-1-propenyl group, a 2-methylallyl group and a 2-butenyl group.

The $C_2$-$C_{20}$ alkynyl group is preferably a $C_2$-$C_{10}$ alkynyl group. Examples of such an alkynyl group include, for example, an ethynyl group, a propynyl group and a butynyl group.

The $C_4$-$C_{20}$ alkyldienyl group is preferably a $C_4$-$C_{10}$ alkyldienyl group. Examples of such an alkyldienyl group include, for example, a 1,3-butadienyl group.

The $C_6$-$C_{18}$ aryl group is preferably a $C_6$-$C_{10}$ aryl group. Examples of such an aryl group include, for example, a phenyl group, a 1-naphthyl group, a 2-naphthyl group, an indenyl group, a biphenyl group, an anthryl group and a phenanthryl group.

The $C_6$-$C_{20}$ alkylaryl group is preferably a $C_6$-$C_{12}$ alkylaryl group. Examples of such an alkylaryl group include, for example, a o-tolyl group, a m-tolyl group, a p-tolyl group, a 2,3-xylyl group, a 2,4-xylyl group, a 2,5-xylyl group, a o-cumenyl group, a m-cumenyl group, a p-cumenyl group and a mesityl group.

The $C_6$-$C_{20}$ arylalkyl group is preferably a $C_6$-$C_{12}$ arylalkyl group. Examples of such an arylalkyl group include, for example, a benzyl group, a phenethyl group, a 1-naphthylmethyl group, a 2-naphthylmethyl group, a 1-phenylethyl group, a phenylpropyl group, a phenylbutyl group, a phenylpentyl group, a phenylhexyl group, a methylbenzyl group, a dimethylbenzyl group, a trimethylbenzyl group, an ethylbenzyl group, a methylphenethyl group, a dimethylphenethyl group and a diethylbenzyl group.

The $C_4$-$C_{20}$ cycloalkyl group is preferably a $C_4$-$C_{10}$ cycloalkyl group. Examples of such a cycloalkyl group include, for example, a cyclopropyl group, a cyclobutyl group, a cyclopentyl group, a cyclohexyl group, a cycloheptyl group and a cyclooctyl group.

The $C_4$-$C_{20}$ cycloalkenyl group is preferably a $C_4$-$C_{10}$ cycloalkenyl group. Examples of such a cycloalkenyl group include, for example, a cyclopropenyl group, a cyclobutenyl group, a cyclopentenyl group, a cyclopentadienyl group and a cyclohexenyl group.

The $C_1$-$C_{20}$ alkoxy group is preferably a $C_1$-$C_{10}$ alkoxy group. Examples of such an alkoxy group include, for example, a methoxy group, an ethoxy group, a propoxy group, a butoxy group and a pentyloxy group.

The $C_6$-$C_{20}$ aryloxy group is preferably a $C_6$-$C_{10}$ aryloxy group. Examples of such an aryloxy group include, for example, a phenyloxy group, a naphthyloxy group and a biphenyloxy group.

The $C_7$-$C_{20}$ alkylaryloxy group is preferably a $C_7$-$C_{12}$ alkylaryloxy group. Examples of such an alkylaryloxy group include, for example, a methylphenyloxy group, an ethylphenyloxy group, a propylphenyloxy group, a butylphenyloxy group, a dimethylphenyloxy group, a diethylphenyloxy group, a dipropylphenyloxy group, a dibutylphenyloxy group, a methylethylphenyloxy group, a methylpropylphenyloxy group and an ethylpropylphenyloxy group.

The $C_2$-$C_{20}$ alkoxycarbonyl group is preferably a $C_2$-$C_{10}$ alkoxycarbonyl group. Examples of such an alkoxycarbonyl group include, for example, a methoxycarbonyl group, an ethoxycarbonyl group, a 2-methoxyethoxycarbonyl group and a t-butoxycarbonyl group.

The optionally substituted amino group listed above encompasses, for example, an amino group, a dimethylamino group, a methylamino group, a methylphenylamino group and a phenylamino group.

The optionally substituted silyl group listed above encompasses, for example, a dimethylsilyl group, a diethylsilyl group, a trimethylsilyl group, a triethylsilyl group, a trimethoxysilyl group, a triethoxysilyl group, a diphenylmethylsilyl group, a triphenylsilyl group, a triphenoxysilyl group, a dimethylmethoxysilyl group, a dimethylphenoxysilyl group and a methylmethoxyphenyl group.

The present invention is characterized by using, as a solvent, an aqueous medium that is extremely inexpensive and safe for handling when compared to other organic solvents. Examples of such an aqueous medium include tap water and distilled water, as well as phosphate buffer, Tris-HCl buffer, acetate buffer, borate buffer, etc.

For use in the reaction of the present invention, amides (e.g., 4-halo-butylamides) and an aqueous medium may be mixed at any ratio. There is no particular limitation on the amount of an aqueous medium to be used, but in general, it is preferably in the range of 1- to 1000-fold excess (by weight), more preferably 2- to 100-fold excess (by weight), relative to Compound (I). To prepare a reaction mixture of these materials, the aqueous medium and amides may be mixed all at once, or alternatively, the amides may be added in divided portions and mixed into a given volume of the aqueous medium.

Also, the reaction mixture may contain an appropriate buffer, e.g., for the purpose of facilitating pH adjustment and/or may contain an appropriate organic solvent, e.g., for the purpose of increasing the solubility of 4-halo-butylamides.

The reaction temperature can be selected as appropriate for the stability of starting materials, etc. For example, it ranges from 30° C. to 100° C., preferably 50° C. to 70° C., and more preferably is 70° C.

The pH at which the reaction is conducted ranges, for example, from 1.0 to 6.0, preferably 1.2 to 5, and more preferably is 3.5. If pH is decreased during the reaction, it is effective to adjust pH with an appropriate alkali (e.g., NaOH, KOH, ammonia, etc.). By way of example, in the reaction where 3-hydroxy-γ-butyrolactone is produced from a 4-halo-3-hydroxybutylamide, 3-hydroxy-γ-butyrolactone can be obtained in higher yield when the reaction mixture is adjusted with an alkali to pH 1.2 to pH 5 than in the case of using no pH adjustment.

Lactones produced and accumulated in the reaction mixture may be collected and purified in a known manner. For example, in the case of producing γ-butyrolactones, if γ-butyrolactones of interest are not water-soluble, they can be obtained by phase separation. In contrast, if γ-butyrolactones of interest are water-soluble, they can be obtained by distillation of water or extraction with an appropriate solvent.

Examples of such an extraction solvent include pyrrolidones, methyl ethyl ketone, methyl isobutyl ketone, cyclohexanone, ethyl acetate, n-butanol, isobutanol, hexane and toluene, which may be selected as appropriate for each case. Since ammonium halides are also generated in the reaction mixture, appropriate salts may be added as needed to separate ammonium halides as a separate phase. This allows phase separation even in the case of using a water-soluble solvent such as acetonitrile or tert-butanol, and is particularly effective in the production of highly hydrophilic γ-butyrolactones.

Also, distillation or other treatments can be used for further purification.

In the present invention, amides (e.g., 4-halo-butylamides) may be obtained using standard procedures for amide synthesis, for example, by ammonia treatment of an acid chloride or an acid anhydride or an ester thereof, dehydration condensation between carboxylic acid and ammonia at an elevated temperature, or hydration of corresponding 4-halo-butyronitriles with a mineral acid or an alkali.

However, hydration of nitriles catalyzed by nitrile hydratase is more preferred because it is excellent in yield and purity.

An explanation will be given of a case where 4-halo-butyronitriles are hydrated.

In this case, nitrile hydratases of any origin may be used as long as they are capable of converting 4-halo-butyronitriles of the following Formula (IV):

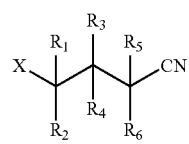

(IV)

into 4-halo-butylamides of the following Formula (II):

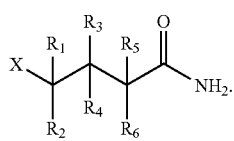

(II)

Examples of microorganisms containing these nitrile hydratases include, for example, those belonging to *Arthrobacter, Brevibacterium, Caseobacter, Corynebacterium, Pseudomonas* or *Rhodococcus*. Specific examples include *Arthrobacter oxydans* IFO 12138, *Brevibacterium helvolum* ATCC 11822, *Corynebacterium flavescens* IAM 1642, *Rhodococcus erythropolis* IFO 12540 and *Rhodococcus erythropolis* IFO 12539, all of which are readily available from the American Type Culture Collection (ATCC), the Institute for Fermentation, Osaka (IFO) or the Institute of Applied Microbiology (IAM), the University of Tokyo.

Further examples include *Arthrobacter* sp. SK103, *Caseobacter* sp. BC23, *Rhodococcus rhodochrous* J-1 [FERM BP-1478: International Patent Organism Depositary, National Institute of Advanced Industrial Science and Technology (Central 6, 1-1-1 Higashi, Tsukuba, Ibaraki 305-8566, Japan), received on Sep. 18, 1987]. *Pseudomonas* sp. BC15-2 [FERM BP-3320: International Patent Organism Depositary, National Institute of Advanced Industrial Science and Technology (Central 6, 1-1-1 Higashi, Tsukuba, Ibaraki 305-8566, Japan), received on Mar. 18, 1991], *Pseudomonas* sp. SK31, *Pseudomonas* sp. SK87, *Pseudomonas* sp. SK13 [FERM BP-3325: International Patent Organism Depositary, National Institute of Advanced Industrial Science and Technology (Central 6, 1-1-1 Higashi, Tsukuba, Ibaraki 305-8566, Japan), received on Mar. 18, 1991], *Rhodococcus* sp. SK70, *Rhodococcus* sp. HR11 and *Rhodococcus* sp. SK49. These microorganisms can be found in Japanese Patent No. 3014171 and those skilled in the art can readily obtain them by reference to this patent document. Moreover, among these microorganisms, *Rhodococcus rhodochrous* J-1 (FERM BP-1478), *Pseudomonas* sp. BC15-2 (FERM BP-3320) and *Pseudomonas* sp. SK13 (FERM BP-3325) have been internationally deposited under the Budapest Treaty. A list of deposit information is as indicated below.

| Microorganism | Labeled as: | Deposit date | Accession No. |
|---|---|---|---|
| *Rhodococcus rhodochrous* J-1 | *Rhodococcus rhodochrous* J-1 | 1987/09/18 | FERM BP-1478 |
| *Pseudomonas* sp. BC15-2 | *Pseudomonas* sp. BC15-2 | 1991/03/18 | FERM BP-3320 |
| *Pseudomonas* sp. SK13 | *Pseudomonas* sp. SK13 | 1991/03/18 | FERM BP-3325 |

In the present invention, microorganisms belonging to any genus listed above can be used either alone or in combination. Alternatively, it is also possible to use mixed microorganisms composed of one or more microorganisms belonging to one genus listed above and one or more microorganisms belonging to another genus listed above.

Moreover, it is possible to use microorganisms transformed with a gene encoding nitrile hydratase which may be taken from the above-listed microorganisms and expressed using an appropriate host-vector system.

By way of example, chromosomal DNA is prepared from the above-listed microorganisms to construct a chromosomal DNA library using an appropriate plasmid vector. Cloning of the nitrile hydratase gene can be accomplished, for example, by colony hybridization or other techniques. PCR primers are designed from a partial amino acid sequence (e.g., N-terminal sequence) of nitrile hydratase and used for PCR with the chromosomal DNA library as a template to obtain a DNA fragment of interest. The nucleotide sequence of DNA encoding nitrile hydratase is determined using a commercially available nucleotide sequencer.

To produce nitrile hydratase using the resulting nitrile hydratase gene, the gene is first linked to an appropriate expression vector to construct a plasmid, which is then introduced into, e.g., an appropriate host to obtain a transformant.

Cloning and gene recombination techniques for the nitrile hydratase gene are well known in the art (see, e.g., Japanese Patent No. 2840253 and 2907479).

Subsequently, upon culturing this transformant, a huge amount of nitrile hydratase is produced in the host cells. Although this enzyme may be used for the conversion reaction in the form of bacterial cells, it is used either as a cell-free extract or in a purified form after crushing the bacterial cells.

In general, any culture medium can be used for culturing the above-listed microorganisms as long as it allows the growth of these microorganisms. Examples of a carbon source available for use include saccharides such as glucose, fructose, sucrose and maltose, organic acids such as acetic acid and citric acid, as well as alcohols such as ethanol and glycerol. Examples of a nitrogen source available for use include naturally-occurring normal nitrogen sources such as peptone, meat extracts, yeast extracts, protein hydrolysates and amino acids, as well as ammonium salts of various inorganic and organic acids. If necessary, the culture medium may further be supplemented, as appropriate, with inorganic salts, trace minerals, vitamins, etc.

To induce higher nitrile hydratase activity, it may also be effective to supplement the culture medium with various nitrile compounds such as n-propionitrile, n-butyronitrile, isobutyronitrile, 4-chloro-3-hydroxybutyronitrile and benzyl cyanide, various amide compounds such as n-propionamide, n-butylamide and isobutylamide, and/or lactam compounds such as γ-butyrolactam, δ-valerolactam and ε-caprolactam, etc.

The above-listed microorganisms may be cultured in accordance with standard procedures, for example, under aerobic conditions for 10 to 180 hours in the range of pH 4 to pH 10 and temperature 10° C. to 40° C. Both liquid and solid culture systems may be used for this purpose.

In the above reaction, nitrile hydratase may be used in a crude or purified form, or alternatively, in the form of a cultured solution of microorganisms, bacterial cells isolated by filtration or centrifugation, crushed bacterial cells, a bacterial cell extract, etc. The enzyme of these forms may further be immobilized on an appropriate carrier (e.g., acrylamide, carragheenan, agarose) or adsorbed on an ion exchange resin or the like. The form to be used is selected as appropriate for the mode of reaction. Possible modes of reaction include those in which the reaction is conducted simultaneously with culturing of microorganisms in the presence of reaction substrates, those in which nitrile hydratase of these forms is suspended in an appropriate aqueous medium, if necessary, and added to reaction substrates, and those in which reaction substrates are added to nitrile hydratase of these forms suspended in an aqueous medium.

Examples of an aqueous medium used for the nitrile hydratase reaction include water as well as other water-based media supplemented with, e.g., buffers containing salts of organic acids, phosphoric acid, boric acid or amines, other salts and/or organic solvents, as needed. There is no particular limitation on the temperature and pH used for the reaction, but they are desirably set within the ranges of 0° C. to 50° C. and pH 3 to pH 10, respectively.

4-Halo-butylamides may be converted into γ-butyrolactones simultaneously with and/or subsequent to the production of 4-halo-butylamides from 4-halo-butyronitriles by the action of nitrile hydratase.

In this case, in order to obtain γ-butyrolactones in high yield, the nitrile hydratase-catalyzed reaction is preferably conducted at 0° C. to 50° C. and, after consuming 4-halo-butyronitriles as much as possible, the temperature is preferably set at 30° C. to 100° C. for the conversion reaction into γ-butyrolactones.

Since the production of 4-halo-butylamides from 4-halo-butyronitriles and the production of γ-butyrolactones from 4-halo-butylamides are both usually exothermic reactions, the reaction vessel should be cooled by means of jackets, internal coils, heat exchangers or the like, if necessary.

Moreover, these reactions, collection, purification and other processes, if any, can be accomplished in either a batch or continuous fashion.

BEST MODE FOR CARRYING OUT THE INVENTION

The present invention will be further described in more detail in the following Examples, which are not intended to limit the scope of the invention.

EXAMPLE 1

An aqueous solution of 4-chloro-3-hydroxybutylamide (34.5% by mass, 100 ml) was reacted in a water bath at 70° C. for 3 hours.

To confirm β-hydroxy-γ-butyrolactone present in the reaction mixture, the reaction mixture was extracted with ethyl acetate and evaporated under reduced pressure to remove the solvent, followed by analysis of the residue by IR, $^1$H-NMR and $^{13}$C-NMR. Each compound was quantified using high performance liquid chromatography under the following conditions.

<Analysis Conditions for High Performance Liquid Chromatography>

Column: Inertsil ODS-3V (4.6 mm ID×25 mm), a product of GL Sciences, Inc.

Mobile phase: 0.1% phosphoric acid in water

Flow rate: 1 ml/min

Column temperature: 40° C.

Detection: differential refractometer (Japan Spectroscopic Co., Ltd.)

As a result, the amount of residual 4-chloro-3-hydroxybutylamide was 1% or less of the initial amount and the yield of β-hydroxy-γ-butyrolactone was 65.2%. The final pH at the completion of the reaction was 0.9. In addition, 4-chloro-3-hydroxybutyric acid was not detected either during or after the reaction.

EXAMPLE 2

An aqueous solution of 4-chloro-3-hydroxybutylamide (34.5% by mass, 100 ml, containing 20 mM phosphate buffer) was reacted in a water bath at 70° C. for 3 hours. During the reaction, a pH controller was used to maintain a pH of 1.2, 2.0, 3.0, 3.5, 4.0, 4.5, 5.0 or 5.5 by adjusting with 24% by mass NaOH. The results were compared to the case where pH was not controlled.

β-Hydroxy-γ-butyrolactone present in the reaction mixture was quantified in the same manner as used in Example 1, indicating that the amount of residual 4-chloro-3-hydroxybutylamide was 1% or less of the initial amount in each case. The yield of β-hydroxy-γ-butyrolactone was as shown in Table 1 below. In the case where pH was not controlled, the final pH at the completion of the reaction was 1.0.

In addition, 4-chloro-3-hydroxybutyric acid was not detected either during or after the reaction in each case.

TABLE 1

| | pH | | | | | | | | |
|---|---|---|---|---|---|---|---|---|---|
| | Uncontrolled | 1.2 | 2 | 3 | 3.5 | 4 | 4.5 | 5 | 5.5 |
| Yield [%] | 65.8 | 69.8 | 73.2 | 79.6 | 85.2 | 78.4 | 73.4 | 66.4 | 56.5 |

EXAMPLE 3

An aqueous solution of 4-chloro-3-hydroxybutylamide (34.5% by mass, 100 ml, containing 20 mM phosphate buffer) was reacted in a water bath at 30° C., 50° C., 70° C. or 100° C. until the amount of residual 4-chloro-3-hydroxybutylamide was reduced to 1% by mole or less of the initial amount. During the reaction, a pH controller was used to maintain a pH of 3.5 by adjusting with 24% by mass NaOH.

β-Hydroxy-γ-butyrolactone present in the reaction mixture was quantified in the same manner as used in Example 1. The yields obtained were as shown in Table 2 below. In addition, 4-chloro-3-hydroxybutyric acid was not detected either during or after the reaction in each case.

TABLE 2

| Reaction temperature [° C.] | 30 | 50 | 70 | 100 |
|---|---|---|---|---|
| Yield [%] | 94.6 | 88.6 | 85.4 | 84.8 |
| Reaction time [hr] | 336 | 15 | 3 | 0.5 |

EXAMPLE 4

An aqueous solution of 4-chloro-3-hydroxybutylamide at a concentration of 11.5%, 23% or 34.5% by mass (100 ml, containing 20 mM phosphate buffer) was reacted in a water bath at 70° C. until the amount of residual 4-chloro-3-hydroxybutylamide was reduced to 1% by mole or less of the initial amount. During the reaction, a pH controller was used to maintain a pH of 3.5 by adjusting with 24% NaOH.

β-Hydroxy-γ-butyrolactone present in the reaction mixture was quantified in the same manner as used in Example 1. The yields obtained were as shown in Table 3 below. In addition, 4-chloro-3-hydroxybutyric acid was not detected either during or after the reaction in each case.

TABLE 3

| Initial concentration [%] | 11.5 | 23 | 34.5 |
|---|---|---|---|
| Yield [%] | 94.8 | 91.3 | 85.2 |
| Reaction time [hr] | 2 | 2.5 | 3 |

EXAMPLE 5

An aqueous solution of 4-chloro-3-hydroxybutylamide (23% by mass, 100 ml, containing 20 mM phosphate buffer) was reacted in a water bath at 70° C. until the amount of residual 4-chloro-3-hydroxybutylamide was reduced to 1% by mole or less of the initial amount. During the reaction, a pH controller was used to maintain a pH of 3.5 by adjusting with 24% NaOH.

After the reaction, methyl ethyl ketone (50 mL) was added to 50 mL of the reaction mixture, followed by vigorous stirring and phase separation to collect the organic layer. This procedure was repeated three times and the resulting organic layer (about 170 mL) was evaporated on a rotary evaporator at a water bath temperature of 60° C. and at 10 torr to remove volatile components, thereby obtaining a clear solution.

β-Hydroxy-γ-butyrolactone was quantified in the same manner as used in Example 1, indicating that the concentration of β-hydroxy-γ-butyrolactone was 94.5% and the water content was 0.2% as measured by the Karl Fischer method.

Upon addition of methyl ethyl ketone (200 mL), this solution became clouded due to precipitates mainly composed of ammonium chloride. The clouded solution was hence filtered under pressure through a 1 μm filter paper and evaporated to remove volatile components in the same manner as described above, thereby obtaining a clear solution. The concentration of β-hydroxy-γ-butyrolactone was 98.1% and the water content was 0.1% or less. The total yield of β-hydroxy-γ-butyrolactone was 64.0%, as calculated from the amount of 4-chloro-3-hydroxybutylamide initially charged.

EXAMPLE 6

An aqueous solution of 4-chloro-3-hydroxybutylamide (23% by mass, 100 ml, containing 20 mM phosphate buffer) was reacted in a water bath at 70° C. until the amount of residual 4-chloro-3-hydroxybutylamide was reduced to 1% by mole or less of the initial amount. During the reaction, a pH controller was used to maintain a pH of 3.5 by adjusting with 24% NaOH.

After the reaction, cyclohexanone (50 mL) was added to 50 mL of the reaction mixture and evaporated on a rotary evaporator at a water bath temperature of 60° C. and at 60 torr to remove water and volatile components. The residue became clouded due to precipitates mainly composed of ammonium chloride, and hence it was filtered under pressure through a 1 μm filter paper and then evaporated on a rotary evaporator at a water bath temperature of 60° C. and at 10 torr to remove residual volatile components.

β-Hydroxy-γ-butyrolactone was quantified in the same manner as used in Example 1, indicating that the concentration of β-hydroxy-γ-butyrolactone was 92.3% and the water content was 0.1% or less. The total yield of β-hydroxy-γ-butyrolactone was 90.4%, as calculated from the amount of 4-chloro-3-hydroxybutylamide initially charged.

EXAMPLE 7

A medium (10 ml, pH 7.2) comprising glucose (10 g/l), $K_2HPO_4$ (0.5 g/l), $KH_2PO_4$ (0.5 g/l), $MgSO_4.7H_2O$ (0.5 g/l), yeast extract (1 g/l) and polypeptone (7.5 g/l) was introduced into a test tube, autoclaved at 121° C. for 15 minutes, and then inoculated with *Rhodococcus rhodochrous* strain J-1, followed by shaking culture at 28° C. for 48 hours. The resulting culture was used as a preliminary culture.

The medium of the above ingredients was further supplemented with urea (15 g/l) and $CoCl_2$ (10 mg/l). The medium thus prepared (100 ml, pH 7.2) was introduced into a 500 ml Erlenmeyer flask, autoclaved at 121° C. for 15 minutes., and then inoculated with the preliminary culture (4 ml), followed by shaking culture at 28° C. for 96 hours.

The bacterial cells thus cultured were collected by centrifugation and suspended in an equal volume of 50 mM phosphate buffer (pH 7.7), followed by centrifugation to collect the cells. The cells were suspended again in the same buffer (10 ml).

An aqueous solution (100 g) containing the bacterial cell suspension thus prepared (10 g), 4-chloro-3-hydroxybutyronitrile (30 g) and 20 mM phosphate buffer (pH 7.0) was prepared and reacted at 30° C. for 1 hour. During the reaction, the temperature of the solution was elevated and hence the solution was cooled with water, as needed, to maintain a temperature of 30° C.

The yield of 4-chloro-3-hydroxybutylamide in the reaction mixture was 99%, as quantified in the same manner as used in Example 1.

This solution was reacted in a water bath at 70° C. for 3 hours. During the reaction, a pH controller was used to maintain a pH of 3.5 by adjusting with 24% by mass NaOH.

β-Hydroxy-γ-butyrolactone present in the reaction mixture was quantified in the same manner as used in Example 1, indicating that the yield calculated from 4-chloro-3-hydroxybutyronitrile was 84.3%. 4-Chloro-3-hydroxybutyronitrile, 4-chloro-3-hydroxybutylamide and 4-chloro-3-hydroxybutyric acid were not detected.

EXAMPLE 8

A methyl ethyl ketone solution (100 ml) containing 11.5% by mass of 4-chloro-3-hydroxybutylamide and 10% by mass of water was reacted in a water bath at 60° C. for 24 hours.

The yield of β-hydroxy-γ-butyrolactone in the reaction mixture was 92%, as quantified in the same manner as used in Example 1. Likewise, the percentage of residual 4-chloro-3- hydroxybutylamide was 5%, and 4-chloro-3-hydroxybutyric acid was not detected either during or after the reaction.

REFERENCE EXAMPLE 1

Under the conditions disclosed in Japanese Patent No. 3014171, *Rhodococcus rhodochrous* J-1 was provided for the production of 4-chloro-3-hydroxybutylamide from 4-chloro-3-hydroxybutyronitrile to confirm whether β-hydroxy-γ-butyrolactone was produced.

A medium of the following composition was dispensed in aliquots of 5 ml into test tubes and sterilized at 120° C. for 15 minutes. Aqueous solutions (5% w/v) of isobutyronitrile and isobutylamide were each sterilized through a membrane filter and added in a volume of 0.1 ml. *Rhodococcus rhodochrous* strain J-1 was inoculated into this medium and cultured with shaking at 30° C. for 72 hours. The bacterial cells were collected by centrifugation and washed with 50 mM phosphate buffer (1.5 ml, pH 7.2), followed by addition of 1 ml of 50 mM phosphate buffer (pH 7.2) containing 88 mM 4-chloro-3-hydroxybutyronitrile. The reaction was continued at 20° C. for 24 hours.

| Medium composition | |
|---|---|
| Glucose | 0.5% |
| $KH_2PO_4$ | 0.05% |
| $K_2HPO_4$ | 0.05% |
| $MgSO_4 \cdot 7H_2O$ | 0.05% |
| Yeast extract | 0.2% |
| Polypeptone | 0.5% |
| $MgCl_2$ | 0.04% |
| KCl | 0.004% |
| $MnSO_4$ | $0.4 \times 10^{-3}$% |
| $FeCl_3$ | $0.6 \times 10^{-5}$% |
| $ZnSO_4$ | $0.3 \times 10^{-4}$% |

The concentration of 4-chloro-3-hydroxybutylamide in the reaction mixture was 77.6 mM, as quantified in the same manner as used in Example 1. In contrast, β-hydroxy-γ-butyrolactone was below the detection limit (1 mM).

EXAMPLE 9

*Rhodococcus rhodochrous* strain J-1 was cultured in the same manner as used in Example 7 to prepare a bacterial cell suspension.

(1 g, chemical purity: 92%) and the bacterial cell suspension (1 g) were added to 18.9 ml of 10 mM phosphate buffer (pH 6.6) and reacted at 5-10° C. for 10 hours. The yield of 4-chloro-3-hydroxybutylamide methacrylate was 99%, as quantified using high performance liquid chromatography under the following conditions.

<Analysis Conditions for High Performance Liquid Chromatography>

Column: Inertsil ODS-3V (4.6 mm ID×25 mm), a product of GL Sciences, Inc.

Mobile phase: 0.1% phosphoric acid and 20% acetonitrile in water

Flow rate: 1 ml/min

Column temperature: 40° C.

Detection: differential refractometer (Japan Spectroscopic Co., Ltd.)

This solution was reacted in a water bath at 70° C. for 7 hours. During the reaction, a pH controller was used to maintain a pH of 2.5 to 3.0 by adjusting with 24% by mass NaOH.

After completion of the reaction, the reaction mixture was extracted twice with an equal volume of toluene and the combined toluene layers were concentrated on a rotary evaporator to give an oily liquid (0.43 g).

The purity of β-hydroxy-γ-butyrolactone methacrylate in the concentrated product was 62%, as quantified by high performance liquid chromatography as described above.

EXAMPLE 10

*Rhodococcus rhodochrous* strain J-1 was cultured in the same manner as used in Example 7 to prepare a bacterial cell suspension.

2-Cyanobenzyl bromide (1 g) and the bacterial cell suspension (1 g) were added to 98 ml of 10 mM phosphate buffer (pH 7.0) and reacted at 10° C. for 3 days.

The yield of 4-chloro-3-hydroxybutylamide in the reaction mixture was 99% or more, as quantified in the same manner as used in Example 9.

This solution was reacted in a water bath at 70° C. for 16 hours. During the reaction, a pH controller was used to maintain a pH of 3.0 by adjusting with 24% by mass NaOH.

After the reaction mixture was extracted with toluene and evaporated under reduced pressure to remove the solvent, the residue was analyzed by IR, $^1$H-NMR and $^{13}$C-NMR to confirm the production of γ-butyrolactones represented by the following Formula (VII):

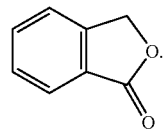

(VII)

The yield was 21%, as quantified in the same manner as used in Example 9.

EXAMPLE 11

An aqueous solution of 4-chloro-2-hydroxybutylamide (10% by mass, 100 ml, containing 20 mM phosphate buffer) was reacted in a water bath at 70° C. for 3 hours. During the reaction, a pH controller was used to maintain a pH of 3.5 by adjusting with 24% by mass NaOH.

After the reaction mixture was extracted with ethyl acetate and evaporated under reduced pressure to remove the solvent, the residue was analyzed by IR, $^1$H-NMR and $^{13}$C-NMR to confirm the production of α-hydroxy-γ-butyrolactone. The amount of residual 4-chloro-3-hydroxybutylamide was 1% or less of the initial amount and the yield was 54%, as quantified in the same manner as used in Example 1.

INDUSTRIAL APPLICABILITY

The present invention provides a method for producing γ-butyrolactones or δ-valerolactones. According to the present invention, the method is industrially useful because these lactones can be produced starting with 4-halo-butylamides or the like, using fewer steps and with a reduced risk of byproduct formation.

What is claimed is:

1. A method for producing a γ-butyrolactone, which comprises:
reacting a 4-halo-butylamide of Formula (II):

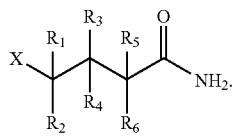

(II)

wherein X represents a halogen atom, and $R_1$ to $R_6$ each independently represents a hydrogen atom or any desired substituent,
with an aqueous medium at a pH of 2 to 4.5 to give a γ-butyrolactone of Formula (III):

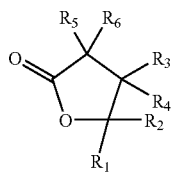

(III)

wherein $R_1$ to $R_6$ each independently represents a hydrogen atom or any desired substituent, and
wherein the 4-halo-butylamide of Formula (II) is a 4-halo-3-hydroxybutylamide; or wherein the 4-halo-butylamide of Formula (II) is produced by nitrile hydratase treatment of a 4-halo-butyronitrile having Formula (IV):

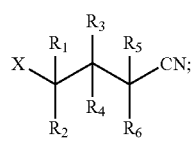

(IV)

wherein X represents a halogen atom, and $R_1$ to $R_6$ each independently represents a hydrogen atom or any desired substituent.

2. The method according to claim 1, wherein the 4-halo-butylamide of Formula (II) is a 4-halo-3-hydroxybutylamide.

3. The method according to claim 1, wherein the 4-halo-butylamide of Formula (II) is produced by nitrile hydratase treatment of a 4-halo-butyronitrile having Formula (IV):

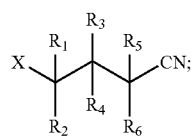

(IV)

wherein X represents a halogen atom, and $R_1$ to $R_6$ each independently represents a hydrogen atom or any desired substituent.

4. The method according to claim 3, wherein nitrile hydratase is produced by a transformant carrying a gene encoding nitrile hydratase.

5. A method for producing a δ-valerolactone, which comprises:
reacting a 5-halo-pentylamide of Formula (V):

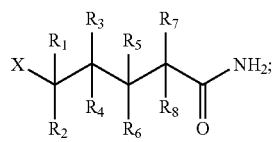

(V)

wherein X represents a halogen atom, and $R_1$ to $R_8$ each independently represents a hydrogen atom or any desired substituent,
with an aqueous medium to give a δ-valerolactone of Formula (VI):

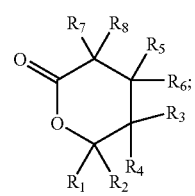

(VI)

wherein $R_1$ to $R_8$ each independently represents a hydrogen atom or any desired substituent.

6. The method according to claim 2, wherein the reaction is carried out at a temperature of 30° C. to 100° C.

7. The method according to claim 5, wherein the reaction is carried out at a temperature of 30° C. to 100° C.

8. A method for producing a lactone, which comprises:
reacting an aqueous medium with an amide compound of Formula (I) to produce a lactone;
wherein Formula (I) is:

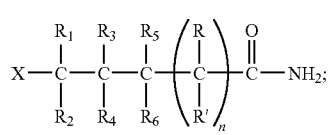

(I)

wherein
X represents a halogen atom; n is an integer of 0, 1 or 2, and R, R' and $R_1$ to $R_6$ each independently represents a hydrogen atom or any desired substituent;
wherein n represents an integer of 1 or 2, or wherein X represents a halogen atom other than iodine, or wherein at least one of R, R', $R_1$, $R_2$, $R_3$, $R_4$, $R_5$, or $R_6$ is not hydrogen.

9. The method of claim 8, wherein n is 1 or 2.

10. The method of claim 9, wherein X represents a halogen atom other than iodine.

11. The method of claim 8, wherein at least one of R, R', $R_1$, $R_2$, $R_3$, $R_4$, $R_5$, or $R_6$ is not hydrogen.

12. The method of claim 8, which is conducted at an acidic pH.

13. The method of claim 8, which is conducted at a pH ranging between 2 and 4.5.

14. A method for producing a ε-caprolactone which comprises:

reacting a 6-halo-hexylamide of Formula (I):

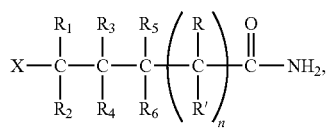

wherein n=2; X represents a halogen atom, and R, R' and $R_1$ to $R_6$ each independently represents a hydrogen atom or any desired substituent;

with an aqueous medium at a pH of 2 to 4.5 to give a ε-caprolactone.

15. The method of claim 14, wherein the 6-halo-hexylamide is produced by nitrile hydratase treatment of the corresponding nitrile.

* * * * *